United States Patent [19]

Schraag

[11] Patent Number: 5,309,918
[45] Date of Patent: May 10, 1994

[54] TRANSDUCER FOR CONVERTING FLOATING GROUND POTENTIAL SIGNALS TO NON-FLOATING SIGNALS AND METHOD OF USE

[75] Inventor: Martin Schraag, Sindelfingen, Fed. Rep. of Germany

[73] Assignee: Hewlett-Packard Company, Palo Alto, Calif.

[21] Appl. No.: 10,498

[22] Filed: Jan. 28, 1993

Related U.S. Application Data

[63] Continuation of Ser. No. 676,884, Mar. 28, 1991, abandoned.

[51] Int. Cl.⁵ .......................................... A61B 5/0428
[52] U.S. Cl. ...................................... 128/696; 128/908; 128/698
[58] Field of Search ............... 128/696, 908, 698, 731, 128/733, 734, 902; 361/38

[56] References Cited

U.S. PATENT DOCUMENTS

| | | | |
|---|---|---|---|
| 3,542,013 | 11/1970 | Stephenson | 128/696 |
| 3,690,313 | 9/1972 | Weppner et al. | 128/908 X |
| 3,915,154 | 10/1975 | Cosentino | 128/908 X |
| 4,191,195 | 3/1980 | Miller | 128/696 |
| 4,243,044 | 1/1981 | Blancke | 128/696 |

Primary Examiner—Lee S. Cohen
Assistant Examiner—Jeffrey R. Jasrzab

[57] ABSTRACT

A transducer for medical monitoring comprises a box (73) which contains a floating section, a non-floating section and a transformer or optical coupler for converting a floating signal into a non-floating signal. The box (73) provides a non-floating signal to an associated monitor. The common-mode rejection ratio is drastically improved, so that electrode gel between the reference electrode and the patient, and possibly even the reference electrode itself, may be omitted.

18 Claims, 8 Drawing Sheets

TRANSDUCER FOR CONVERTING FLOATING GROUND POTENTIAL SIGNALS TO NON-FLOATING SIGNALS AND METHOD OF USE

This is a continuation of application Ser. No. 676,884, filed Mar. 28, 1991, now abandoned.

FIELD OF THE INVENTION

The present invention generally relates to the field of transducers, and more particularly relates to transducers adapted for use with a medical monitor, e.g., a fetal monitor.

BACKGROUND OF THE INVENTION

The present invention particularly relates to electrocardiogram (ECG) transducers for a fetal monitor, wherein the ECG may either be a direct ECG of the fetus or a maternal ECG. A fetal monitor measures and records the fetal beat-to-beat heart rate (FHR) and uterus activity (toco). Simultaneous assessment of both parameters facilitates an accurate determination of the fetal condition. The FHR may be obtained with a scalp electrode after rupture of the membranes; prior to this time an ultrasound (US) transducer placed externally on the pregnant woman's abdomen may be used. Uterus activity may likewise either be recorded with an intrauterine pressure transducer or by an external tocodynamometer (a tension-measuring device). Some external methods for recording the FHR depend on the placement of the transducers. E.g., the accuracy of the ultrasound method is dependent on the proper orientation of the ultrasound beam; if the beam is not properly focussed on the fetal heart, the maternal heart rate may be recorded instead of the fetal heart rate. It is therefore advantageous to record the maternal heart rate and to compare it with the fetal heart rate.

The present invention deals particularly with the fetal and/or maternal ECG electrodes of such fetal monitors, and in fact the invention was made during the design process of a fetal monitor. It is understood, however, that the invention is not limited to such an application, but rather relates to all types of transducers with galvanic coupling to the patient, including, e.g., electrocardiogram transducers, electroencephalogram transducers, electromyogram transducers and electrooculogram transducers.

A common characteristic of the transducers mentioned above (i.e., transducers with galvanic coupling to the patient) is that they provide an electrical connection between the patient and the monitor. For reasons of patient safety, the patient ground potential (floating ground) must therefore be galvanically separated from the ground potential of the associated monitor (non-floating ground). This problem has been solved in the past with separation circuitry on a printed circuit board inside the monitor, e.g., with transformers or optoelectronic couplers.

The use of separation circuitry placed inside the monitor for separating the patient's floating ground potential from the monitor's non-floating ground potential has several drawbacks. One drawback is that, since there is capacitive coupling between the mains and the patient and between non-floating ground and the patient, an AC voltage of the mains frequency (50 Hz/60 Hz) is coupled into the transducer cable. This common mode voltage impairs the results of the measurement. Moreover, since the fetal QRS complexes must be recorded very accurately and their signal level is typically quite low (e.g., 20 $\mu$V peak to peak in some cases), fetal monitoring requires a high common mode rejection ratio (CMRR). A reliable signal can be obtained only if the common mode rejection ratio is greater than 150 dB. It is technologically possible to improve the CMRR by approximately 30 dB by means of a suitable notch filter; the remaining 120 dB must be attained by other measures.

One method for attaining the necessary CMRR is to apply a predefined potential to the patient, i.e., to drive the patient to this potential. The attainable CMRR is around 103 dB; the remaining 17 dB necessary for a CMRR of 120 dB can be obtained by means of an active variable-gain amplifier (common-mode amplifier) which drives the electrode. For stability reasons, this common-mode amplifier can usually not compensate for considerably more than 20 dB. This technique is widely used in medical monitoring of adults, e.g., for recording the maternal heart rate in fetal monitoring applications. As the active electrode driving the patient is usually an electrode attached to the right leg of the patient, it is also known as "right leg drive." To acquire a direct ECG of the fetus, a silver plate is attached to the mother's body. This method has some serious disadvantages, including:

1. The method works properly only if the right leg electrode contains silver, which makes the electrode expensive, and if electrode gel is used between the electrode and the patient's skin (to reduce the resistance between electrode and skin). The gel is uncomfortable, expensive and requires periodic, difficult cleaning of the equipment.

2. An additional electrode, which is required only to compensate for an imperfect measurement technique, must be applied. This is particularly disturbing if the electrodes do not remain attached to the patient for long periods (such as in intensive care monitoring), but rather are changed frequently (as in fetal screening). It is also disturbing if the other electrodes are not attached to the patient's body (as with a fetal scalp electrode), in which case the right leg electrode must be handled separately from the measuring electrodes.

An important goal of electrode design is therefore to make the electrode gel unnecessary, and, in some cases, to altogether avoid the right leg electrode. This goal has been extremely difficult to achieve. E.g., when the reference electrode (right leg drive) is omitted, the CMRR is approximately 61 dB, instead of the required 120 dB; on the other hand, when the reference electrode is used and the electrode gel omitted, a common-mode amplifier with an amplification of at least 40 dB at 50/60 Hz is required, which requires difficult measures to keep the amplifier stable under all operating conditions.

Due to the safety risks associated with common-mode signals, transducers which generate a floating potential (such as ECG transducers) and transducers which generate a non-floating potential (such as toco transducers) cannot not be connected with the associated monitor via a single cable. This is a significant limitation, as there are many applications employing multiple transducers where it would be desirable to have only one cable leading to the monitor, e.g., direct fetal ECG and toco monitoring, or maternal ECG and ultrasound monitoring.

The schematic diagram in FIG. 1a illustrates the problem underlying the present invention. Patient 1 is being monitored; an electrode 2 with an electrical connection to the patient is used (electrode 2 represents e.g., an electrocardiogram electrode). There is a certain capacity $C_1$ between the patient's body and the mains voltage $U_s$. Likewise, there exists a capacity $C_2$ between the patient and ground. This situation generates a common-voltage mode voltage $U_{p0}$ at electrodes 2. (It is a "common-mode" because it is the same for other electrodes.) Common-mode voltage $U_{p0}$ impairs the measurement.

The situation is also shown, in the form of an equivalent circuit, in FIG. 1b. The circuit of FIG. 1b can be transformed into the circuit of FIG. 1c, i.e., common-mode voltage $U_{p0}$ can be calculated as $$U_{p0} = \frac{C_1}{C_1 + C_2} U_S \quad (1)$$

$C_1$ is typically in the range of 20 pF, whereas $C_2$ is typically approximately 200 pF. For mains voltage $U_s$ between 100 V and 240 V, common-mode voltages $U_{p0}$ between 9.1 V and 21.8 V are obtained.

FIG. 2 is a schematic diagram illustrating an artificial measurement using two electrodes 5, 6. Common-mode voltage $U_{p0}$ (indicated by voltage source 3) is applied to capacitor 4 ($C_p$) that represents the internal resistance of the voltage source (i.e., $C_p$ is equal to the parallel combination of $C_1$ and $C_2$ of FIGS. 1a–1c), thus generating a voltage $U_p$. Voltage $U_p$ is a common-mode voltage present at both electrodes; as shown below, $U_p$ is not equal to $U_{p0}$. Electrode 6 contains an imbalancing impedance $Z_{im}$ consisting of a 51.1 kΩ resistor 7 and a 47 nF capacitor 8. $Z_{im}$ is prescribed by international standards, e.g., IEC 62D, to simulate the different electrode impedances in an artificial environment.

The two electrode signals are fed to a difference amplifier 9. The input resistance of this amplifier is represented by resistors 10 and 11. The input resistance $R_i$ at both electrode inputs is approximately equal, about 10MΩ.

The circuit 12 surrounded by dashed lines operates at floating potential, indicated by arrow 13, as opposed to earth potential 14. The floating circuit therefore has a capacitive coupling to ground (i.e., earth potential), which coupling is represented by capacitor 15 of capacitance C. Capacitance C results from the cable and circuit capacitance to ground and is approximately 200 pF. Capacitor 4 ($C_p$) and capacitor 15 (C) constitute a capacitive voltage divider, which is why voltages $U_{p0}$ and $U_p$ are not equal.

The CMRR of the circuit of FIG. 2 is calculated according to the following equation:

$$CMRR = -20 * \log\left(\frac{i_{CM} * Z_{im}}{U_p}\right) \quad (2)$$

wherein $i_{CM}$ is the common-mode current flowing through the two electrodes. $i_{CM}$ is approximately equal to two times the current through each of the electrodes, i.e., $$i_{cm} \approx 2*i_1 \approx 2*i_2 \quad (3)$$

Using eq. (2), the circuit of FIG. 2 reveals $$CMRR = -20 * \log\left[\frac{Z_{im}}{\frac{R_i}{2} - j\frac{1}{\omega C}}\right] \quad (4)$$

which yields, assuming a mains frequency of 60 Hz, a capacitance C of 200 pF and internal resistance $R_i$ of 10 MΩ, a common-mode rejection ratio of $$CMRR \approx 61 \text{ dB} \quad (5)$$

Since 59 dB of the 120 dB required to obtain a reliable signal is missing, the circuit of FIG. 2 is not suitable for monitoring a patient.

FIG. 3 is a schematic circuit similar to FIG. 2, but including a reference electrode. In addition to the components shown in FIG. 2 (which are labeled with the same reference numbers in FIG. 3), the circuit of FIG. 3 comprises a common-mode amplifier 16 connected via an impedance $Z_{LP}$ to an additional reference electrode. The reference electrode is typically applied to the patient's leg.

Impedance $Z_{LF}$ may be characterized by the parallel combination of a resistor 17 and a capacitor 18 and represents the impedance between the patient's body and the reference electrode. If the reference electrode comprises silver and electrode gel is used, then $Z_{LP}$ is given by $$Z_{LP} \approx Z_{im} \quad (6)$$

If the reference electrode is directly coupled to floating ground, the ratio $R_i : 2 : Z_{LF}$ determines the relation $(i_1+i_2)/i_3$ ($i_3$ represents the current through the reference electrode); the common-mode current fraction $(i_1+i_2)$ will therefore decrease (assuming a mains frequency of 60 Hz) by the factor $$\frac{Z_{LP}}{R_i/2} = \frac{1}{132} \quad (7)$$

which corresponds to a further common-mode rejection of 42 dB. If the active amplifier (common-mode amplifier 16) contributes another 20 dB, the total common-mode rejection ratio is $$CMRR_{total} = 61 \text{ dB} + 42 \text{ dB} + 20 \text{ dB} = 123 \text{ dB} \quad (8)$$

which is, according to the requirement of 120 dB, a sufficient value. This, however, requires the use of electrode gel at the reference electrode, which has the disadvantages mentioned above. If no gel is used, the common-mode amplifier must provide an amplification of 40 dB, which, due to stability requirements, is difficult to achieve.

A further problem arises if the monitor provides a single input port for alternative insertion of a transducer which provides non-floating potentials and a transducer which provides floating potentials, e.g., the ultrasound transducer and the scalp electrode, each of which is used to detect fetal heart rates. As these transducers are not used together at the same time, it is possible to insert them alternatively into the same port, or connector, thus saving a second connector. To ensure proper operation, the connector must be divided into a floating part and a non-floating part. This in turn means that the shield of the ECG cable cannot be fed through the connector, resulting in capacitive leakage around the connector. Common-mode currents that cannot be compensated by a common-mode amplifier can flow through this leakage. The attainable CMRR is around 90 dB in this case. Although it is possible to attain another 30 dB by additional measures, these require either components with extremely small tolerances or additional time-consuming adjustments during the manufacturing process and are therefore very costly. This problem is schematically illustrated in FIG. 4. If one uses a connector for insertion of a floating (e.g., ECG) as well as a non-floating (e.g., ultrasound) transducer, the shield of the ECG cable cannot be fed through the connector, thus generating a capacitive leakage which cannot be offset by an active amplifier. This capacitive leakage is indicated in FIG. 4 by capacitors 19, 20 and 21, each of which has a value $C_c$ of approximately 2 pF.

It is therefore a goal of the present invention to provide a transducer which makes it unnecessary to use electrode gel and, at least in some instances, to avoid the reference electrode altogether. A further goal of the present invention is to provide a means for safely combining transducers providing floating potentials with transducers providing non-floating potentials. A still further goal of the present invention is to provide a means for avoiding capacitive leakage around the input port of the monitor to which the transducer(s) is (are) connected.

SUMMARY OF THE INVENTION

The present invention achieves the aforementioned goals by providing apparatuses and methods that provide non-floating output signals to the monitors to which the transducers are coupled. A transducer in accordance with the invention comprises a first section having a non-floating ground potential, the first section adapted to be coupled to a monitor; a second section having a floating ground potential, the second section adapted to be coupled to a sensor which produces floating signals; and conversion means for converting floating signals generated by the second section into non-floating signals.

In a first preferred embodiment of the invention the conversion means comprises at least one transformer. This embodiment may also comprise load modulation means for providing to the transformer a transformer current which is modulated with a signal generated by the second section.

In a second preferred embodiment of the invention the transducer further comprises frequency modulation means for providing to the conversion means a signal which is modulated with a signal generated by the second section. According to the invention, the transformer includes a primary winding coupled to the first, non-floating, section and a secondary winding coupled to the second, floating, section. In addition, the connection between the primary winding and a cable connecting the transducer to a monitor is essentially without further electronic components between the primary winding and cable (see, e.g., FIG. 6). Floating signals are thus convertible to non-floating signals at or near the patient.

In a third preferred embodiment of the invention the conversion means comprises an optical coupler for converting a signal generated by the second section into an optical signal. This embodiment may also comprise frequency modulation means for providing to the conversion means a signal which is modulated with a signal generated by the second section.

In another embodiment, the transducer further comprises an analog-to-digital converter coupled to the first section for digitalizing non-floating signals generated by the first section.

In yet another embodiment, the transducer further comprises a third section having a floating ground potential and adapted to be coupled to at least one sensor, and means for converting a floating signal generated by the third section into a non-floating signal.

The present invention also encompasses a transducer in combination with a medical monitor having a non-floating ground potential and at least one sensor having a floating ground potential. A specific embodiment comprises a non-floating section, a floating section adapted to be coupled to the sensor, conversion means for converting floating signals generated by the floating section into non-floating signals, and a cable adapted to be connected between the non-floating section and the monitor.

A method, in accordance with the present invention, for providing signals to a monitor comprises the steps of generating a floating signal indicative of a condition being monitored, converting the floating signal into a non-floating signal, and providing the non-floating signal to the monitor.

BRIEF DESCRIPTION OF THE DRAWINGS

FIG. 1b depicts an equivalent circuit representing the circuit of FIG. 1a.

DETAILED DESCRIPTION OF THE PREFERRED EMBODIMENTS

Figure 1A:
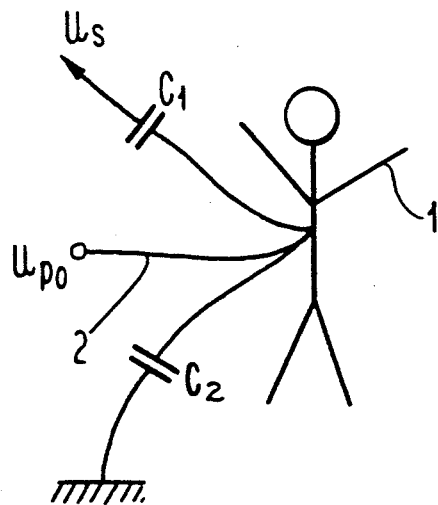
FIG. 1a depicts a patient's capacitive coupling.
Figure 1B:
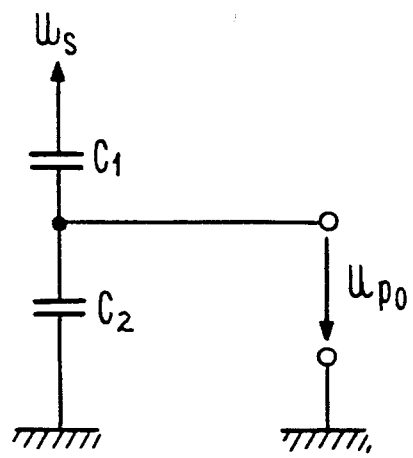
Figure 1C:
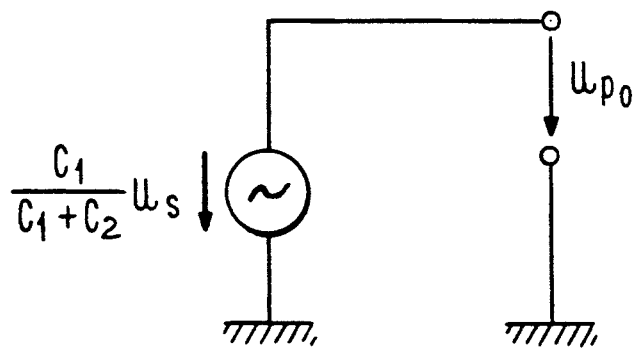
FIG. 1c depicts an equivalent circuit representing the circuit of FIG. 1b.
Figure 2:
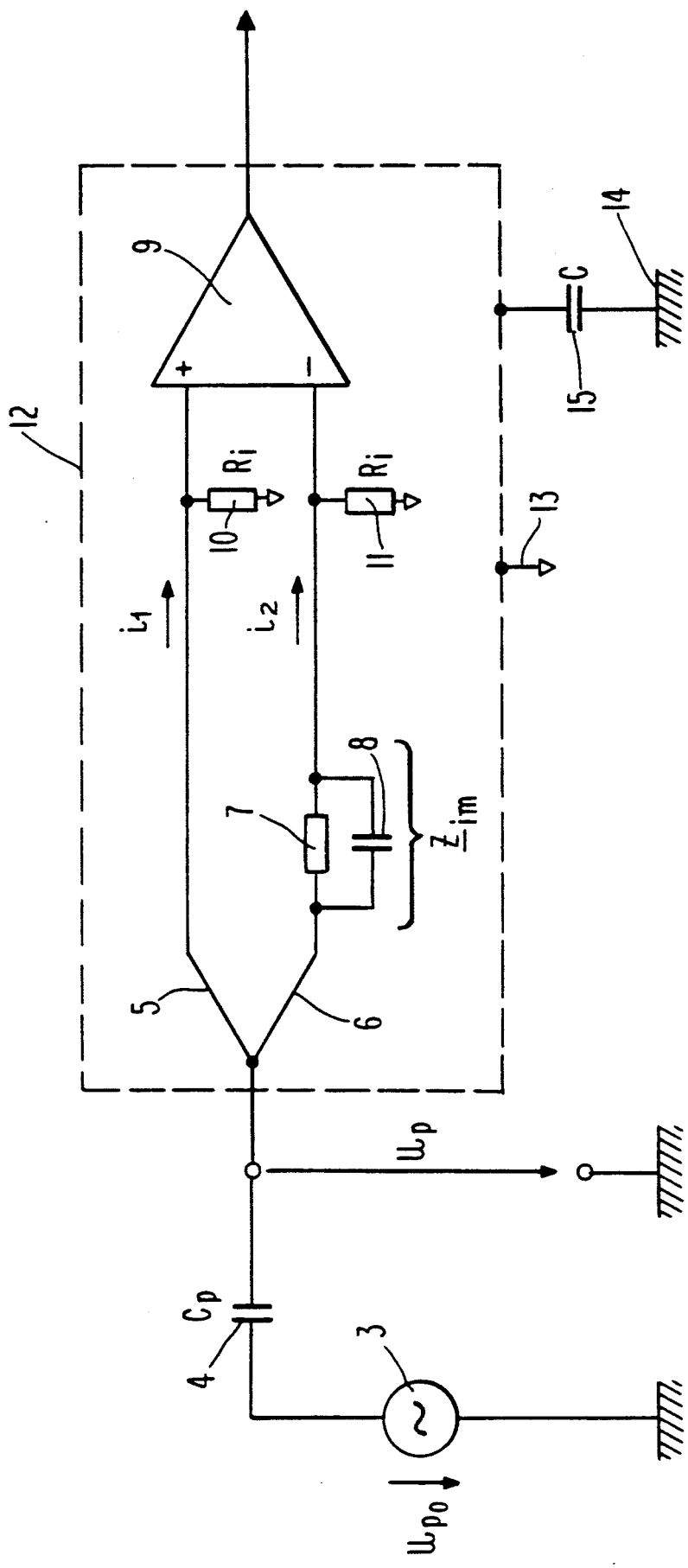
FIG. 2 depicts a measurement configuration having two cables.
Figure 3:
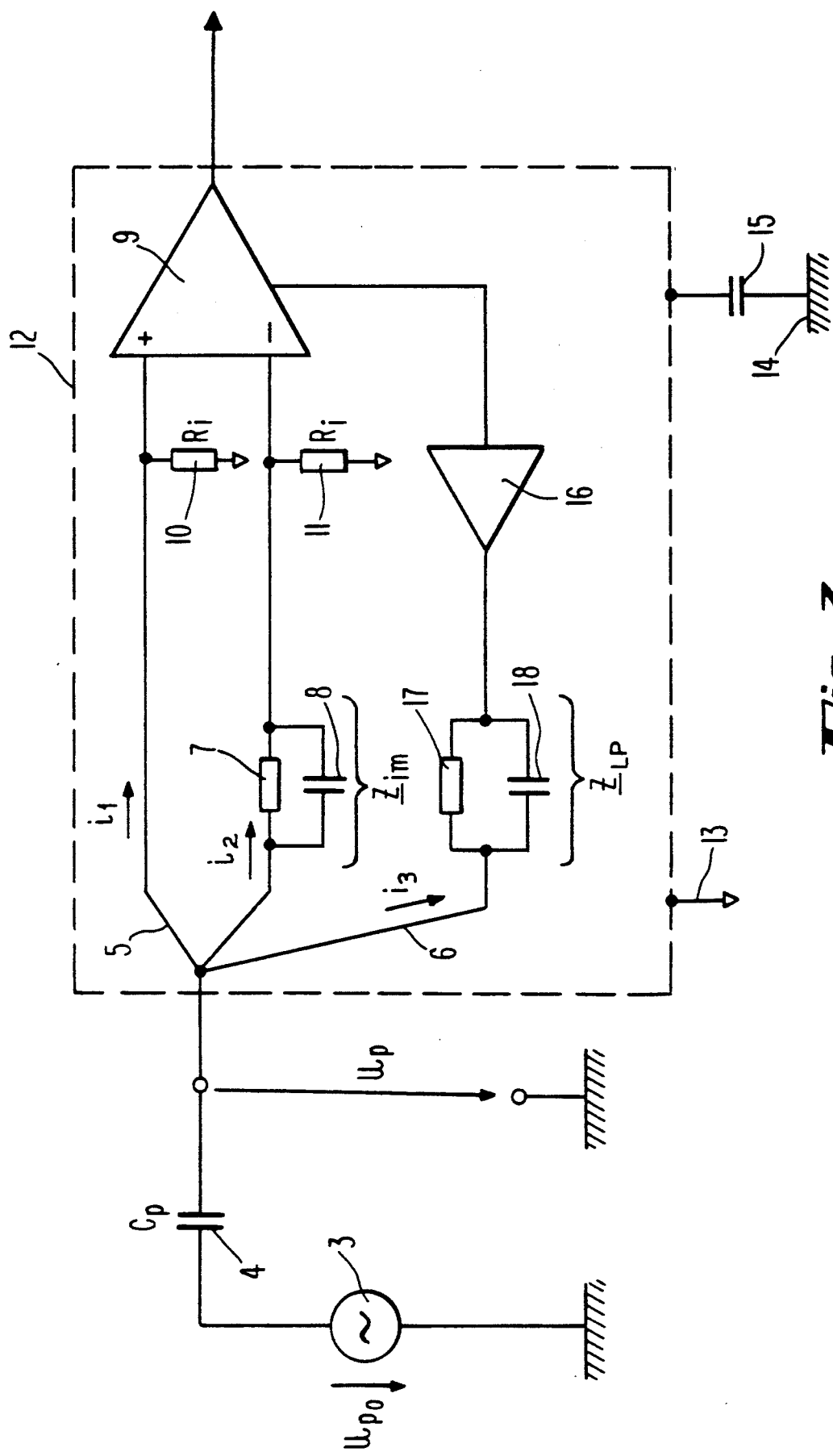
FIG. 3 depicts a measurement configuration having a reference electrode.
Figure 4:
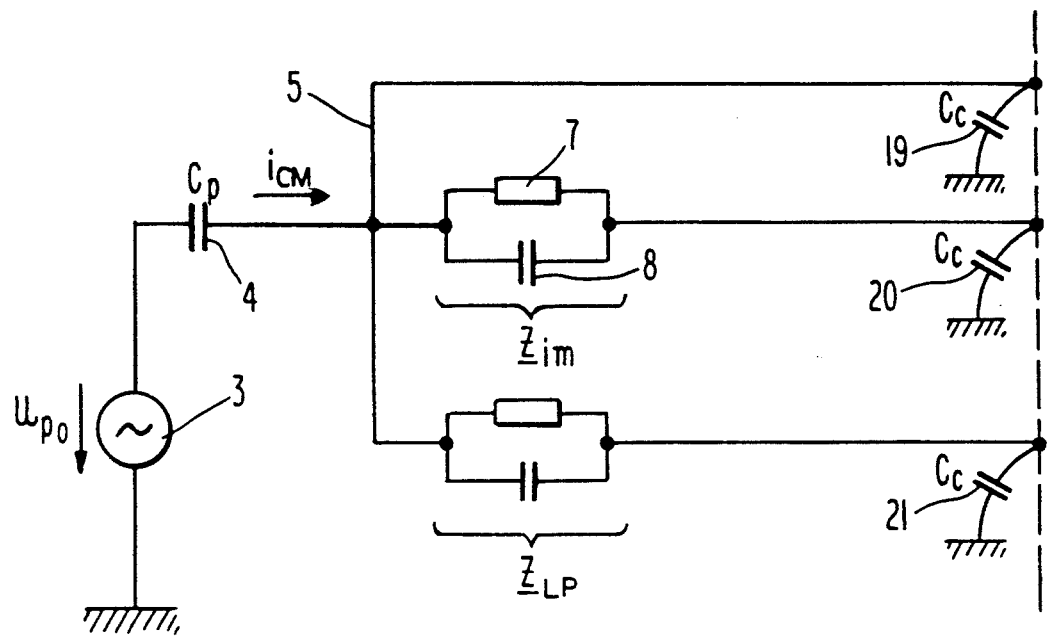
FIG. 4 schematically depicts the consequences of capacitive leakage in the connector.

Transducers embodying of the present invention include a box containing floating/non-floating separation circuitry. The box is adapted to be positioned near the patient, e.g., fixed to the patient's skin or bed. A sensor (e.g., an ECG electrode) is coupled to the floating section of the box via a fixed or detachable cable or wire. The non-floating section is coupled via a fixed or detachable cable with a monitor. An advantage of this configuration is that the floating connection between the sensor and the box is very short, which greatly reduces the capacitive coupling between the patient and ground. Measurements reveal that the capacity is reduced from the 200 pF of the prior art transducers to approximately 2 pF; i.e., its sensitivity to common mode signals is reduced roughly by a factor of 100, or 40 dB. Furthermore, the capacity between the patient and mains is also reduced.

The invention therefore makes it is possible to avoid the appliance of electrode gel to the reference electrode and still obtain a reliable result. This increases the usefulness of the transducer, as measurements may be performed more easily and complex cleaning of the transducer is unnecessary. In addition, the reference electrode may be avoided entirely in some cases. As discussed above, the basic common mode rejection ratio of a system without a reference electrode is in the range of 61 dB. If an additional rejection of 40 dB is added, a CMPR of about 101 dB is attained. It is possible to obtain the remaining 19 dB with additional electronic measures, so that neither a reference electrode nor electrode gel is required. This additional circuitry may be omitted, however, if there is an easy way of applying a reference electrode. This is a matter of design choice for the particular application. In particular, if a fetal or maternal electrocardiogram is recorded, the box will be attached (e.g., by means of an adhesive tape) to the maternal body. According to an advantageous embodiment of the present invention, the box comprises a ground plate at its bottom side. This ground plate acts as a reference electrode. As the box must be attached to the mother's body anyway, and as no electrode gel has to be applied to the ground plate, there is no inconvenience for the nurse, as there is no need for her (or him) to even note that there is a reference electrode.

Since the cable from the box to the monitor provides non-floating potentials, the invention also makes it possible to connect multiple transducers to the monitor using a single cable. For example, the non-floating sections of a maternal ECG transducer and an ultrasound transducer may be connected to the same cable, which is in turn fed to the monitor. Another example is the combination of the non-floating sections of a direct fetal ECG transducer (spiral electrode) and a toco transducer. (Neither the ultrasound transducer nor the toco transducer is electrically coupled to the patient, therefore they each provide non-floating signals.) Thus, the confusion and handling disadvantages encountered with multiple cables can be avoided. Moreover, the above-described monitor input port leakage problem is solved: As the cables between the respective transducer boxes and the monitor all provide non-floating potentials, a special connector for floating potentials is unnecessary. It is even possible to use unshielded cables.

Another advantage of the present invention is safety. If, e.g., the cable is damaged by mechanical forces, the patient is not placed in danger, even if the damaged cable is connected with mains or another voltage source, as there is no conducting connection between the non-floating potential in the cable and the floating potential of the sensor.

The usefulness of a transducer in accordance with the present invention may be further increased if a batching roller is used to keep the cable in place. The cable may also be shielded to minimize electromagnetic interference.

Figure 5:
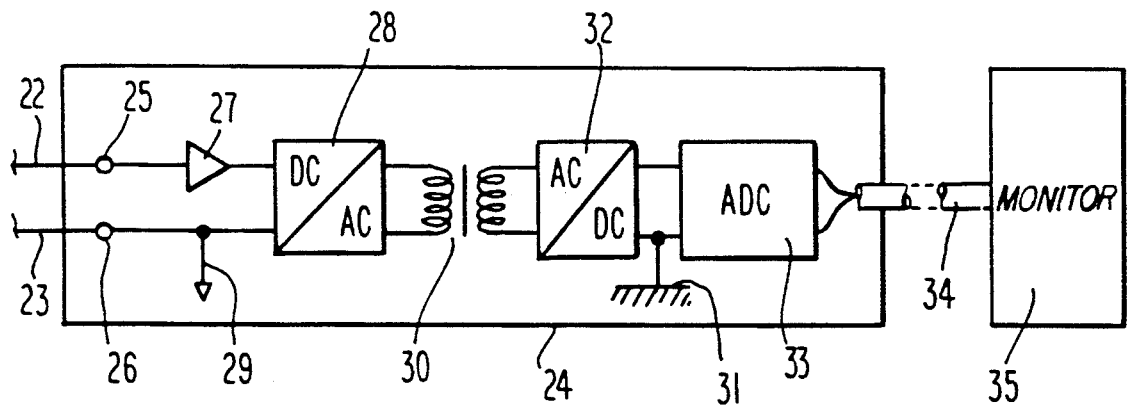
FIG. 5 depicts a first embodiment of the present invention.

FIG. 5 depicts a first embodiment of the present invention. Two electrodes, indicated by wires 22 and 23, are fed to a box 24 and connected to electrical contacts 25 and 26; the connection is preferably releasable to facilitate electrode exchange. Box 24 is adapted to be attached to the patient by, e.g., a belt or adhesive tape. The box contains a floating section and a non-floating section. In the embodiment of FIG. 5, the floating section comprises a pre-amplifier 27 and a DC/AC converter 28. Arrow 29 indicates floating ground. The AC signal is fed to a transformer 30, which ensures the galvanic separation between floating ground in the floating section and non-floating ground 31 in the non-floating section. The non-floating section comprises an AC/DC converter 32 and an analog-to-digital converter (ADC) 33. The digital signal generated by ADC 33 is fed, via cable 34 (preferably a releasable cable) to a monitor 35.

Figure 6:
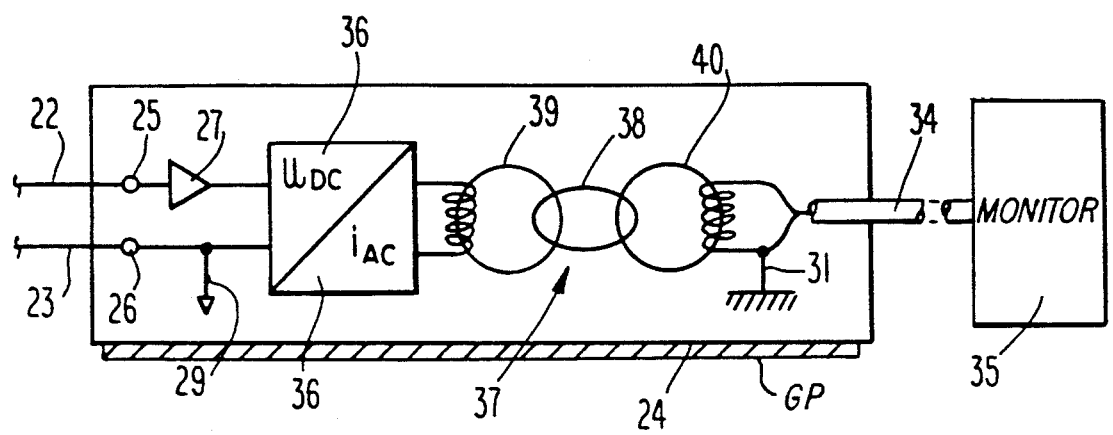
FIG. 6 depicts a second embodiment of the present invention.

A more sophisticated embodiment of the present invention is depicted in FIG. 6. Electrodes 22 and 23 are connected via preamplifier 27 to a $U_{DC}/I_{AC}$-Converter S6 (i.e., a dc voltage to ac current converter). The power consumption of the floating section is proportional to the amplitude of the signal generated by the electrodes. (This is also called load modulation.) The alternating current signal is fed to a transformer 37 comprising a short-circuit transformer (ring 38) with magnetic toroidal cores 39 and 40. The signal is then fed via cable 34 to monitor 35.

The capacitance of transformer 37 is only about 3 pF, which leads to a basic CMRR of approximately 91 dB. If an additional rejection of 20 dB is obtained with a common-mode amplifier, a CMRR of 111 dB is obtained; another 9 dB may easily be achieved by additional electronic measures or a reference electrode. The crucial point is that, even if a reference electrode is used, the 9 dB rejection can be obtained without electrode gel. The reference electrode may be incorporated as an electrical contact at the bottom side of box 24 (e.g., a ground plate GP). Since the box must be applied to the patient anyway, and as no gel is necessary, the reference contact will not complicate handling.

Figure 7:
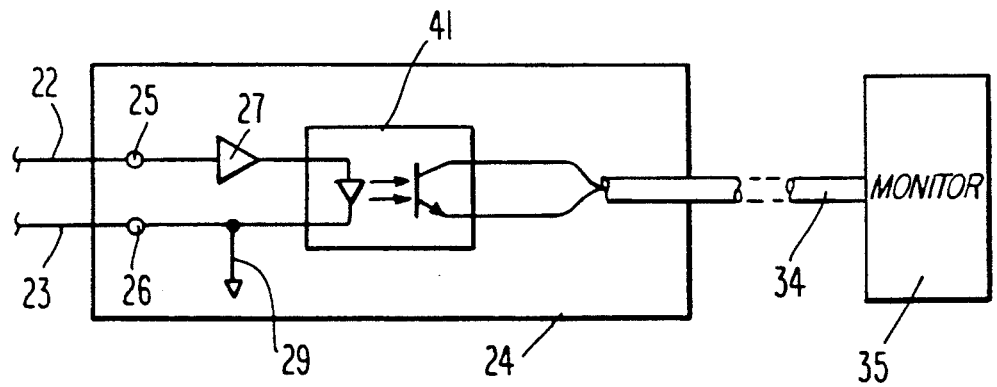
FIG. 7 depicts a third embodiment of the present invention.

A third embodiment of the invention is depicted in FIG. 7. In this embodiment, the electrode signal is fed to an optical coupler 41. Frequency modulation, as opposed to load modulation, is used here. In addition, this embodiment requires a path (not shown) for the transmission of electrical power to the floating section. Patient isolation is nearly perfect in this environment.

Figure 8:
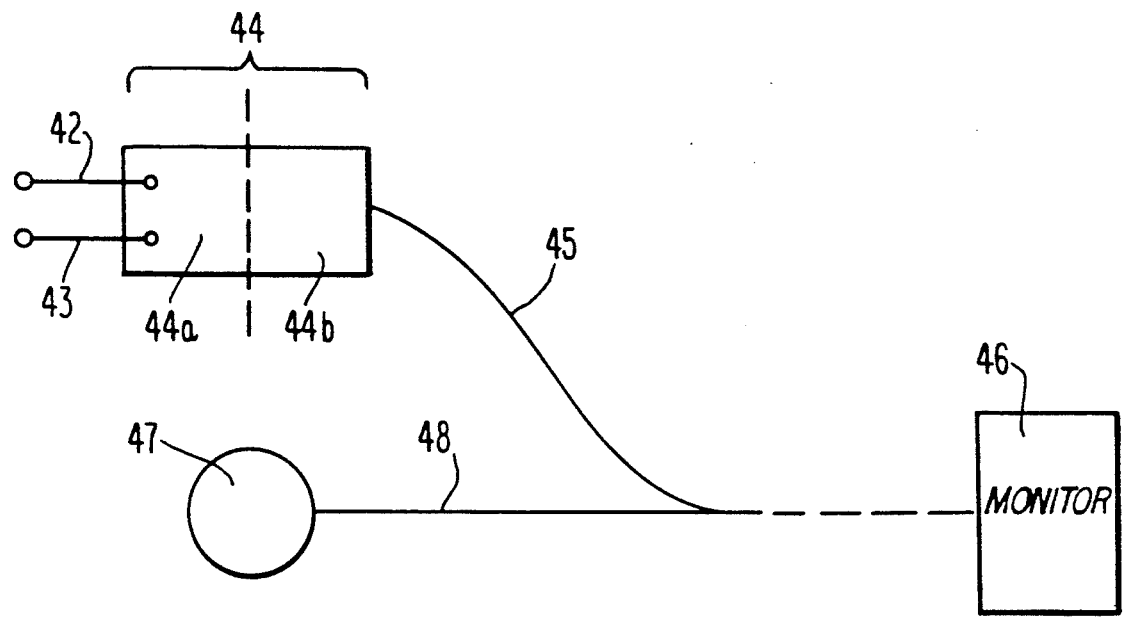
FIG. 8 schematically depicts the coupling of a floating transducer and a non-floating transducer with a V-connector.

FIG. 8 depicts an example of how multiple sensors can be combined in order to reduce the number of cables between the patient and monitor. Two ECG electrodes 42 and 43 are fed to the floating section 44a of box 44. The non-floating section 44b of this box is connected via a cable 45 to monitor a 46. Another transducer 47 (e.g., an ultrasound transducer) delivers non-floating signals to the monitor 46. Cable 48 of transducer 47 is combined with cable 45 by means of a V-connector, which is possible only if both cables 45, 48 provide non-floating signals. Note that, in the prior art, wherein the ECG cable transmits floating signals, a combination of floating and non-floating signals into the same cable is not possible.

Figure 9:
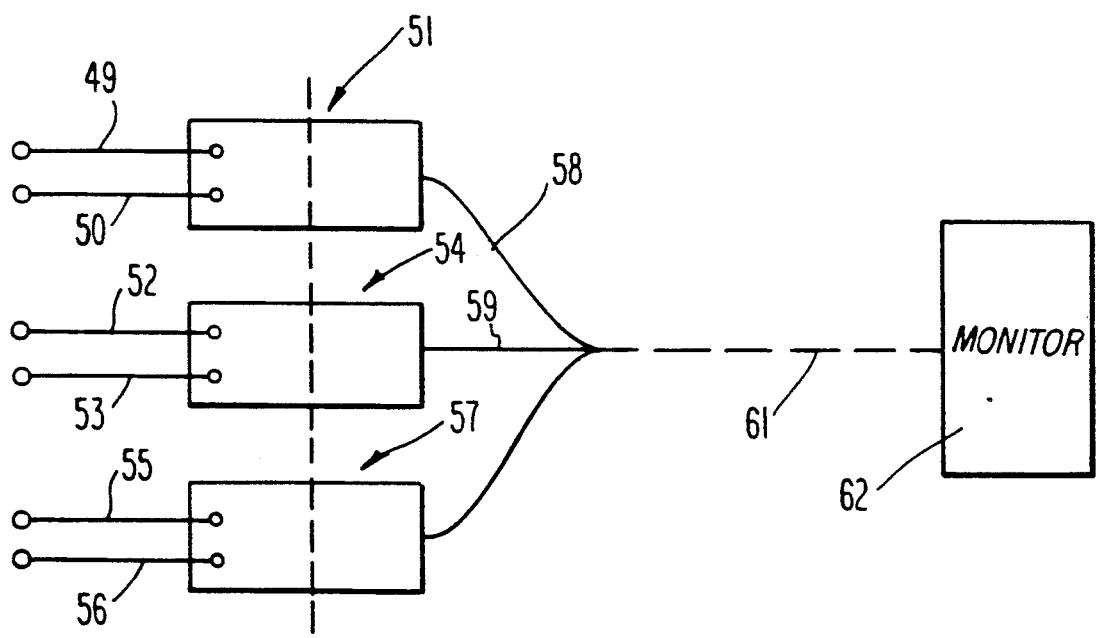
FIG. 9 schematically depicts the coupling of a multiplicity of floating transducers with a V-connector.

The idea underlying the arrangement of FIG. 8 may be expanded, as shown in FIG. 9. In FIG. 9 a multiplicity of transducers is connected via a single cable to a monitor 62. This arrangement will work whether the associated sensors generate floating signals or not, as their associated boxes all deliver non-floating signals. In the example of FIG. 9, two ECG electrodes 49 and 50 (e.g., for a maternal ECG) are connected with box 51;

second ECG electrodes 52 and 53 (e.g., for the direct ECG of a first fetus) are connected to box 54; and third ECG electrodes 55 and 56 (e.g., for the direct ECG of a second fetus) are connected to box 57. Each respective box 51, 54, 57 contains a floating and a non-floating section, so that the signals provided to cables 58, 59 and 60 are all non-floating, thus making it possible to combine cables 58, 59, 60 into a single cable 61 leading to monitor 62.

Figure 10:
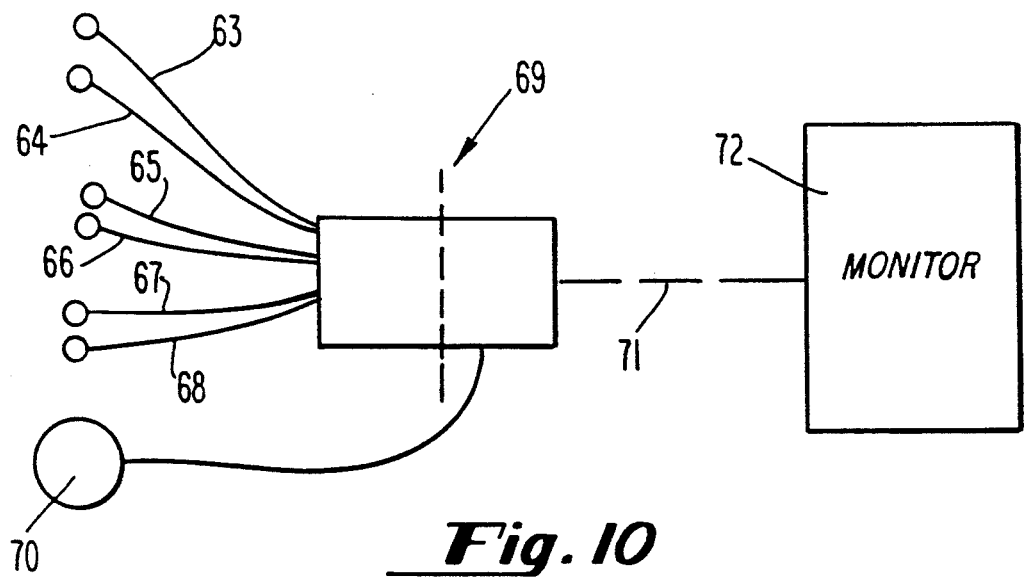
FIG. 10 schematically depicts the coupling of a multiplicity of floating sensors and a non-floating sensor to a monitor.

Another arrangement is depicted in FIG. 10. Several ECG electrodes (electrode pairs 63 and 64, 65 and 66 and 67 and 68) are connected to the floating section of box a 69. A non-floating transducer 70 (e.g., ultrasound or toco transducer) is connected to the non-floating section of box 69. A single cable 71 connects the box with monitor a 72.

Figure 11:
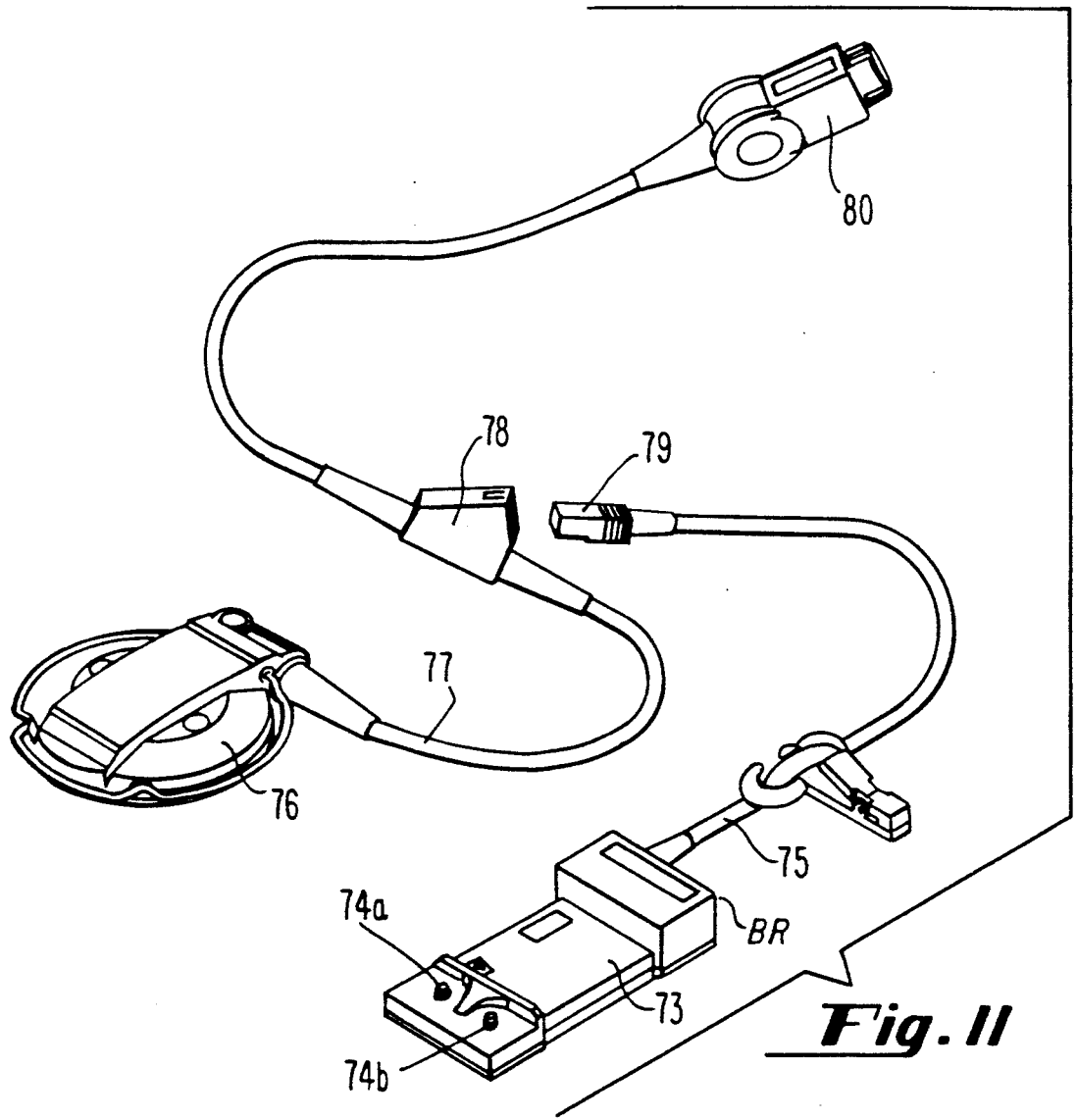
FIG. 11 depicts a perspective view of a maternal ECG/ultrasound transducer combination for use with a fetal monitor.

FIG. 11 depicts the use of the invention in the context of a fetal monitor. Box 73 contains the floating/non-floating sections; it comprises two pins 74a, 74b for the releasable attachment of maternal ECG electrodes. Cable 75 therefore carries non-floating signals. The bottom of box 73 carries a ground plate (not shown) which acts as a reference electrode and which does not require electrode gel to be applied to it. A second transducer 76 provides ultrasound signals. This measurement technique needs no galvanic coupling to the patient and therefore generates non-floating signals per se. Its cable 77 comprises a V-connector 78 for the insertion of plug 79 which is part of cable 75. Plug 80 is adapted to be inserted into an appropriate connector of a monitor, and plug 79 is adapted to be inserted into a V-connector 78. It is therefore possible to record both the maternal ECG as well as ultrasound signals via a single cable to the monitor. Of course the ultrasound signal may be recorded without the maternal ECG. In addition, an arrangement (not shown) similar to the one shown in FIG. 11 could, e.g., combine direct fetal ECG and toco measurements.

Figure 12:
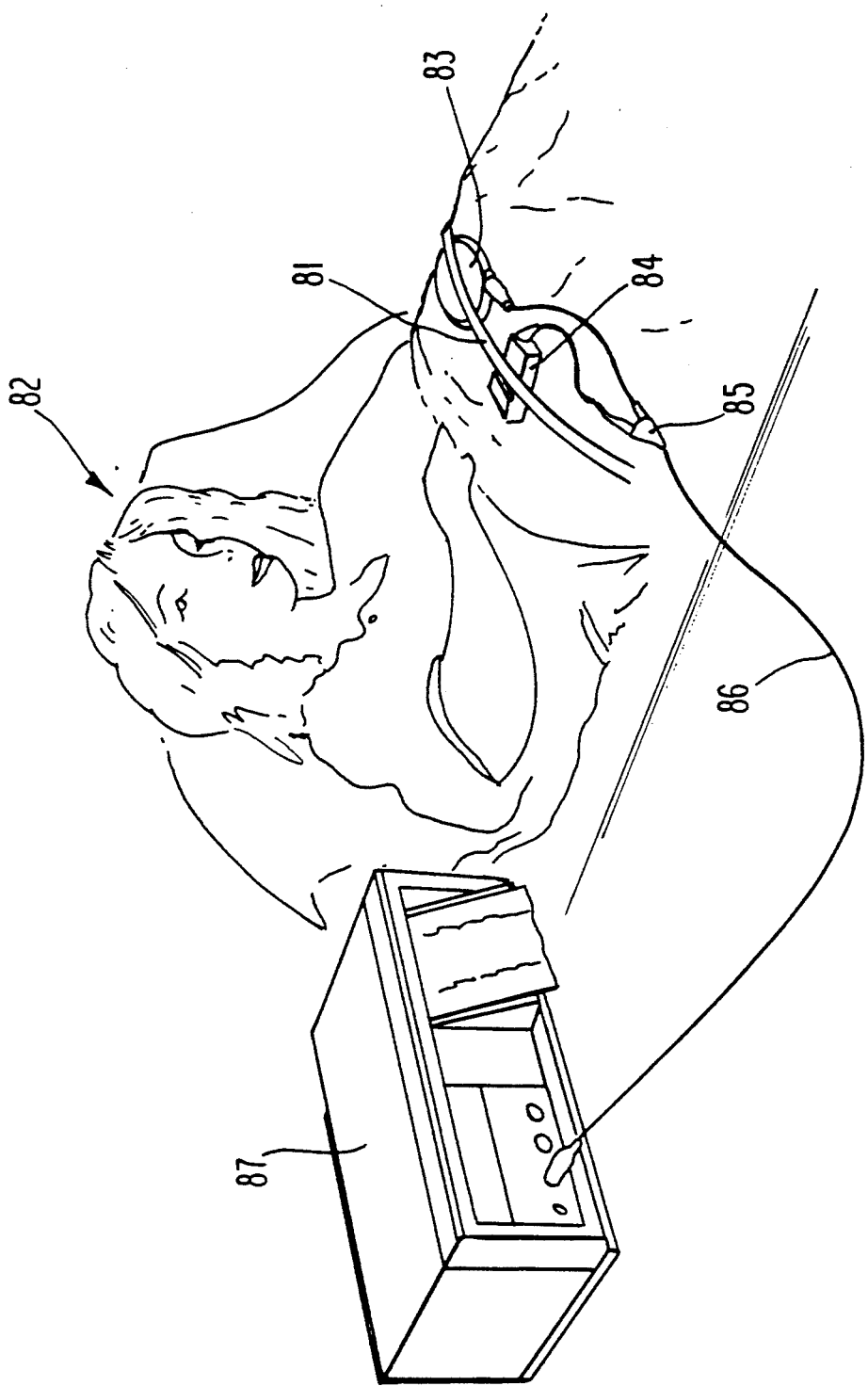
FIG. 12 depicts the use of the transducer of FIG. 11 in a clinical application.

FIG. 12 depicts the embodiment of FIG. 11 in a clinical environment. A belt 81 is applied around the abdomen of pregnant woman 82. This belt keeps transducer 83 (an ultrasound transducer) and box 84 in place. Their respective cables are combined in V-connector 85. A single cable 86 leads to a fetal monitor 87.

The true scope of the present invention (which is set forth in the claims) is not limited to the preferred embodiments described above. For example, although the preferred embodiments of the present invention have been described in the context of a fetal monitor, wherein the transducer is a maternal electrocardiogram transducer or a direct fetal electrocardiogram transducer, it may also be used in other environments.

What is claimed is:

1. A transducer, comprising:
   a box and cable means for electrically coupling said box to a medical monitor, said box containing:
   (a) a first section having a non-floating ground potential, said first section electrically coupled to said cable means;
   (b) a second section having a floating ground potential, said second section comprising means for electrically coupling said floating ground potential to a sensor which produces floating signals; and
   (c) conversion means coupled to said first and second sections for converting floating signals provided to said second section into non-floating signals, said conversion means comprising a transformer having a primary winding coupled to said first section and a secondary winding coupled to said second section, the connection between said primary winding and cable means consisting essentially of a direct electrical connection without further electronic components between said primary winding and cable means, whereby floating signals are convertible to non-floating signals at or near a patient.

2. The transducer recited in claim 1, wherein said transformer comprises magnetic toroidal cores.

3. The transducer recited in claim 1, further comprising load modulation means for providing to said transformer a transformer current which is modulated with a signal generated by said second section.

4. The transducer recited in claim 1, further comprising frequency modulation means for providing to said conversion means a signal which is modulated with a signal generated by said second section.

5. The transducer recited in claim 1, further comprising:
   a third section having a floating ground potential, said third section adapted to be coupled to at least one sensor; and
   means for converting a floating signal generated by said third section into a non-floating signal.

6. A transducer in combination with a medical monitor having a non-floating ground potential and at least one sensor having a floating ground potential, the transducer comprising the box interfacing said sensor to said monitor, said box containing:
   (a) a non-floating section;
   (b) a floating section electrically coupled to said sensor;
   (c) conversion means for converting floating signals generated by said sensor into non-floating signals; and
   (d) a cable connected between said non-floating section and said monitor, said conversion means comprising a transformer having a primary winding coupled to said first section and a secondary winding coupled to said second section, the connection between said primary winding and said cable consisting essentially of a direct electrical connection without further electronic components between said primary winding and said cable, whereby floating signals are convertible to non-floating signals at or near a patient.

7. The combination recited in claim 6, characterized in that said transformer is a short-circuit transformer having magnetic toroidal cores.

8. The combination recited in claim 6, further comrpising load modulation means for providing to said transformer a transformer current which is modulated with a signal generated by said floating section.

9. The combination recited in claim 6, further comprising multiple floating sections coupled with multiple sensors.

10. The combination recited in claim 6, further comprising at least one further sensor coupled to the non-floating section.

11. The combination recited in claim 6, wherein said cable provides connection means for connection of a second cable, whereby a second sensor may be coupled to said monitor.

12. The combination recited in claim 6, further comprising batching roller means for holding said cable in place.

13. The combination recited in claim 6, wherein said cable contains a shield.

14. The combination recited in claim 6, wherein said sensor and monitor comprise means for producing an electrocardiogram of a fetus.

15. The combination recited in claim 14, further comprising ground plate means for electrically connecting said box and said floating section to a maternal abdomen.

16. A method for providing signals to a medical monitor, comprising the steps of:
 (a) generating a floating signal indicative of a condition of a patient being monitored;
 (b) converting said floating signal, at or near the patient and remote from the monitor, into a non-floating signal; and
 (c) providing said non-floating signal to the monitor directly, without further processing of said non-floating signal outside of said monitor and without passing said non-floating signal through any electronic components.

17. The method recited in claim 16, further comprising the step of modulating said floating signal prior to converting it into a non-floating signal.

18. A transducer, consisting essentially of:
 a box and cable means for electrically coupling said box to a medical monitor, said box containing:
 (a) a first section having a non-floating ground potential, said first section electrically coupled to said cable means;
 (b) a second section having a floating ground potential, said second section comprising means for electrically coupling said floating round potential to a sensor which produces floating signals; and
 (c) conversion means coupled to said first and second sections for converting floating signals provided to said second section into non-floating signals, said conversion means comprising a transformer having a primary winding coupled to said first section and a secondary winding coupled to said second section, the connection between said primary winding and cable means consisting essentially of a direct electrical connection without further electronic components between said primary winding and cable means, whereby floating signals are convertible to non-floating signals at or near a patient.

* * * * *